(12) United States Patent
Narimatsu

(10) Patent No.: US 7,361,148 B2
(45) Date of Patent: Apr. 22, 2008

(54) CUFF VOLUMETRIC PULSE WAVE OBTAINING APPARATUS, CUFF VOLUMETRIC PULSE WAVE ANALYZING APPARATUS, PRESSURE PULSE WAVE OBTAINING APPARATUS, AND PRESSURE PULSE WAVE ANALYZING APPARATUS

(75) Inventor: Kiyoyuki Narimatsu, Komaki (JP)

(73) Assignee: Colin Medical Techology Corporation, Aichi-Ken (JP)

(*) Notice: Subject to any disclaimer, the term of this patent is extended or adjusted under 35 U.S.C. 154(b) by 840 days.

(21) Appl. No.: 10/756,408

(22) Filed: Jan. 14, 2004

(65) Prior Publication Data
US 2004/0158162 A1     Aug. 12, 2004

(30) Foreign Application Priority Data
Jan. 24, 2003   (JP)   ............................. 2003-016797

(51) Int. Cl.
*A61B 5/02* (2006.01)
(52) U.S. Cl. ................... 600/494; 600/490; 600/493
(58) Field of Classification Search ................ 600/481, 600/485, 490–504
See application file for complete search history.

(56) References Cited

U.S. PATENT DOCUMENTS

| | | | | |
|---|---|---|---|---|
| 3,090,377 | A | * 5/1963 | Salisbury et al. | ........... 600/490 |
| 5,099,853 | A | 3/1992 | Uemura et al. | |
| 5,289,823 | A | * 3/1994 | Eckerle | ...................... 600/492 |
| 5,746,698 | A | * 5/1998 | Bos et al. | .................... 600/493 |
| 5,790,032 | A | * 8/1998 | Schmidt | .................. 340/573.4 |
| 5,830,148 | A | 11/1998 | Inukai et al. | |
| 6,036,651 | A | 3/2000 | Inukai et al. | |
| 6,122,537 | A | * 9/2000 | Schmidt | ...................... 600/407 |
| 6,413,224 | B1 | 7/2002 | Ogura et al. | |
| 6,527,725 | B1 | 3/2003 | Inukai et al. | |

FOREIGN PATENT DOCUMENTS

| | | |
|---|---|---|
| JP | A 5-200030 | 8/1993 |
| JP | A 7-275214 | 10/1995 |
| JP | A 9-215664 | 8/1997 |
| JP | A 11-318838 | 11/1999 |
| JP | A 2000-33078 | 2/2000 |
| WO | WO 88/04910 | 7/1988 |

\* cited by examiner

*Primary Examiner*—Charles A. Marmor, II
*Assistant Examiner*—Navin Natnithithadha
(74) *Attorney, Agent, or Firm*—Oliff & Berridge, PLC

(57) ABSTRACT

A subject evaluation value measuring apparatus 10, functioning as a cuff volumetric pulse wave obtaining apparatus, includes a pulse wave determining device (i.e., a cuff volumetric pulse wave determining device) 52 that determines, using an inverse transfer function 1H(f), stored in a ROM (i.e., an inverse transfer function memory) 42, that corresponds to a pre-determined transfer function H(f) between input, i.e., pressure pulsation produced in a cuff 20, and output, i.e., pressure pulsation detected by a pressure sensor 24, a no-delay cuff volumetric pulse wave $P_K(t)$ having substantially no delay of transmission, based on an actual cuff pulse wave signal SM outputted by the pressure sensor 24. The thus determined cuff volumetric pulse wave $P_K(t)$ is free of waveform distortion and accordingly enjoys high accuracy.

16 Claims, 5 Drawing Sheets

CUFF VOLUMETRIC PULSE WAVE OBTAINING APPARATUS, CUFF VOLUMETRIC PULSE WAVE ANALYZING APPARATUS, PRESSURE PULSE WAVE OBTAINING APPARATUS, AND PRESSURE PULSE WAVE ANALYZING APPARATUS

BACKGROUND OF THE INVENTION

1. Field of the Invention

The present invention relates to a pulse wave obtaining apparatus which obtains a cuff volumetric pulse wave produced in a cuff worn on a limb of a living subject, or a pressure pulse wave produced in an artery of a living subject, and a pulse wave analyzing apparatus which analyzes a cuff volumetric pulse wave or a pressure pulse wave.

2. Related Art Statement

A cuff pulse wave as pressure oscillation produced in a cuff (i.e., an inflatable bag) wound around a limb of a living person, in synchronism with heartbeat of the subject, is known as one of a plurality of sorts of information related to person's circulatory organ. Since this pressure oscillation represents the change of volume of blood in person's tissues, including arteries, around which the cuff is wound, it is called a cuff volumetric pulse wave. In addition, a pressure pulse wave as pressure pulsation produced in an artery of a person, in synchronism with heartbeat of the person, is also known as another sort of circulatory organ-related information. Information contained by the cuff volumetric pulse wave or the pressure pulse wave is analyzed to evaluate the circulatory organ or make a diagnosis on the same. For example, Patent Document 1 (International Patent Application Publication WO 88-04910 or its corresponding U.S. Pat. No. 5,099,853) teaches that a maximum magnitude of a heartbeat synchronous pulse of a pulse wave is used to estimate a systolic blood pressure of a person; Patent Document 2 (Japanese Patent Publication No. 2000-33078 or its corresponding U.S. Pat. No. 6,527,725) teaches that respective rising points of respective heartbeat synchronous pulses of respective pulse waves obtained from two different regions of a person are used to obtain pulse wave propagation velocity-related information representing arteriosclerosis of the person, and that the wave propagation velocity-related information and, optionally, a pulse area ratio and a pulse period are used to estimate a blood pressure (e.g., a systolic blood pressure) of the person; Patent Document 3 (Japanese Patent Publication No. 11-318838 or its corresponding U.S. Pat. No. 6,036,651) teaches that a pulse area ratio VR as the ratio of pulse area to pulse period is used to evaluate the blood outputting function of the heart of a person; Patent Document 4 (Japanese Patent Publication No. 7-275214 or its corresponding U.S. Pat. No. 6,413,224) teaches that a waveform characteristic value such as a pulse amplitude, a maximum slope SLOPE of a rising portion of a pulse, a pulse sharpness % MAP as the ratio of height position of gravity center of pulse area to pulse amplitude, a rising-portion percentage value as the ratio of rising-portion time to pulse period, and a peak index PI as the ratio of time between maximum point to next peak point to pulse period is used to determine an estimated blood pressure of a person; an augmentation index AI as the ratio of amplitude of reflected wave to amplitude of incident wave is used to indicate arteriosclerosis of a person; Patent Document 5 (Japanese Patent Publication No. 5-200030) teaches that a blood pressure ratio as the ratio of maximum magnitude of a pulse after change of posture to maximum magnitude of a pulse before the change of posture is used to indicate autonomic imbalance; and Patent Document 6 (Japanese Patent Publication No. 9-215664 or its corresponding U.S. Pat. No. 5,830,148) teaches that fluctuations of respective maximum magnitudes of respective heartbeat synchronous pulses that are iteratively determined are used to indicate activity of autonomic nerve.

Meanwhile, the cuff volumetric pulse wave is obtained by extracting, from an electric signal representing the cuff pressure detected by a pressure sensor connected to a cuff via, e.g., a rubber tube, an oscillatory component representing the pulse wave, using a band-pass filter. Therefore, when the pulse wave propagates through air in the cuff or the rubber tube that has a great compliance, the waveform of the pulse wave is distorted. Thus, the extracted cuff volumetric pulse wave may not be sufficiently accurate, and the evaluation of person's circulatory organ and/or the diagnosis made on the same based on the pulse wave may not be sufficiently accurate, either. In addition, in the case where the cuff volumetric pulse wave is used, on the assumption that it represents the change of intra-arterial pressure, to evaluate the circulatory organ or make diagnosis on the same, the waveform of the pulse wave is additionally distorted by the skin and/or subcutaneous tissue of the person, and the above-indicated problem is worsened.

SUMMARY OF THE INVENTION

It is therefore an object of the present invention to provide a cuff volumetric pulse wave obtaining apparatus which can obtain an accurate cuff volumetric pulse wave from a living subject, a cuff volumetric pulse wave analyzing apparatus which can analyze an accurate cuff volumetric pulse wave obtained from a living subject and evaluate the circulatory organ of the subject and/or make a diagnosis on the same, a pressure pulse wave obtaining apparatus which can obtain an accurate pressure pulse wave from a living subject, and a pressure pulse wave analyzing apparatus which can analyze an accurate pressure pulse wave obtained from a living subject and evaluate the circulatory organ of the subject and/or make a diagnosis on the same.

According to a first aspect of the present invention, there is provided an apparatus for obtaining a cuff volumetric pulse wave, comprising a cuff adapted to be worn on a limb of a living subject so that a pressure pulsation is produced in the cuff, a pressure sensor which is connected to the cuff, and which detects, as an actual cuff volumetric pulse wave, a pressure oscillation transmitted thereto from the cuff; an inverse transfer function memory which stores an inverse transfer function corresponding to a transfer function between pressure pulsation as input and pressure oscillation as output, and a cuff volumetric pulse wave determining means for determining a no-delay cuff volumetric pulse wave having substantially no delay of transmission, based on the actual cuff volumetric pulse wave detected by the pressure sensor using the inverse transfer function stored by the inverse transfer function memory.

According to the first aspect of the present invention, the cuff volumetric pulse wave determining means determines, using the inverse transfer function, stored by the inverse transfer function memory, that corresponds to the predetermined transfer function between input, i.e., pressure pulsation produced in the cuff and output, i.e., pressure pulsation detected by the pressure sensor, the no-delay initial cuff volumetric pulse wave, based on the actual cuff volumetric pulse wave detected by the pressure sensor. Thus, the present apparatus can obtain the accurate cuff volumetric pulse wave that has substantially no distortion and enjoys high accuracy.

According to a second aspect of the present invention, there is provided an apparatus for analyzing a cuff volumetric pulse wave obtained from a living subject, comprising the cuff volumetric pulse wave obtaining apparatus according to the first aspect of the present invention; and a pulse wave analyzing means for analyzing the no-delay cuff volumetric pulse wave obtained by the cuff volumetric pulse wave obtaining apparatus, and thereby determining at least one of a blood pressure, a pulse wave propagation velocity, an arteriosclerosis evaluation index, and an autonomic nerve evaluation value of the subject.

According to the second aspect of the present invention, the pulse wave analyzing means analyzes the no-delay cuff volumetric pulse wave obtained by the cuff volumetric pulse wave obtaining apparatus according to the first aspect of the invention, and thereby determines at least one of the blood pressure, the pulse wave propagation velocity, the arteriosclerosis evaluation index, and the autonomic nerve evaluation value of the subject. That is, at least one of the blood pressure, the pulse wave propagation velocity, the arteriosclerosis evaluation index, and the autonomic nerve evaluation value of the subject is determined by analyzing the accurate cuff volumetric pulse wave. Thus, an accurate evaluation of the circulatory organ of the subject and/or an accurate diagnosis on the same can be made.

According to a third aspect of the present invention, there is provided a method of obtaining a cuff volumetric pulse wave with an apparatus including a cuff adapted to be worn on a limb of a living subject so that a pressure pulsation is produced in the cuff, a pressure sensor which is connected to the cuff, and which detects, as an actual cuff volumetric pulse wave, a pressure oscillation transmitted thereto from the cuff, an inverse transfer function memory which stores an inverse transfer function corresponding to a transfer function between pressure pulsation as input and pressure oscillation as output, and a cuff volumetric pulse wave determining a no-delay cuff volumetric pulse wave having substantially no delay of transmission based on the actual cuff volumetric pulse wave detected by the pressure sensor and the inverse transfer function stored by the inverse transfer function memory, the method comprising: (a) a step of determining the inverse transfer function corresponding to the transfer function, and storing the determined inverse transfer function in the inverse transfer function memory, and (b) a step of determining, using the inverse transfer function stored by the inverse transfer function memory, the no-delay cuff volumetric pulse wave having substantially no delay of transmission, based on the actual cuff volumetric pulse wave detected by the pressure sensor.

According to the third aspect of the present invention, after the inverse transfer function corresponding to the transfer function between input, i.e., pressure pulsation produced in the cuff and output, i.e., pressure pulsation detected by the pressure sensor, is determined, and stored by the inverse transfer function memory, the no-delay, initial cuff volumetric pulse wave is determined, using the inverse transfer function stored by the inverse transfer function memory, based on the actual cuff volumetric pulse wave detected by the pressure sensor. The thus determined cuff volumetric pulse wave has substantially no distortion and enjoys high accuracy.

According to a fourth aspect of the present invention, there is provided a method of obtaining a cuff volumetric pulse wave with an apparatus including a cuff adapted to be worn on a limb of a living subject so that a pressure pulsation is produced in the cuff, a pressure sensor which is connected to the cuff, and which detects, as an actual cuff volumetric pulse wave, a pressure oscillation transmitted thereto from the cuff, an inverse transfer function memory which stores an inverse transfer function corresponding to a transfer function between pressure pulsation as input and pressure oscillation as output, a cuff volumetric pulse wave determining means for determining a no-delay cuff volumetric pulse wave having substantially no delay of transmission based on the actual cuff volumetric pulse wave detected by the pressure sensor and the inverse transfer function stored by the inverse transfer function memory, and a pulse wave analyzing means for analyzing the no-delay cuff volumetric pulse wave determined by the cuff volumetric pulse wave determining means, the method comprising: (a) a step of determining the inverse transfer function corresponding to the transfer function, and storing the determined inverse transfer function in the inverse transfer function memory, (b) a step of determining, using the inverse transfer function stored by the inverse transfer function memory, the no-delay cuff volumetric pulse wave having substantially no delay of transmission, based on the actual cuff volumetric pulse wave detected by the pressure sensor, and (c) a step of analyzing the determined no-delay cuff volumetric pulse wave, and thereby determining at least one of a blood pressure, a pulse wave propagation velocity, an arteriosclerosis evaluation index, and an autonomic nerve evaluation value of the subject.

According to the fourth aspect of the present invention, after the inverse transfer function corresponding to the transfer function between input, i.e., pressure pulsation produced in the cuff and output, i.e., pressure pulsation detected by the pressure sensor, is determined, and is stored by the inverse transfer function memory, the no-delay, initial cuff volumetric pulse wave is determined, using the inverse transfer function stored by the inverse transfer function memory, based on the actual cuff volumetric pulse wave detected by the pressure sensor. The thus determined cuff volumetric pulse wave has substantially no distortion and enjoys high accuracy. In addition, the no-delay cuff volumetric pulse wave is analyzed to determine at least one of the blood pressure, the pulse wave propagation velocity, the arteriosclerosis evaluation index, and the autonomic nerve evaluation value of the subject. Thus, the accurate cuff volumetric pulse wave is analyzed and accordingly an accurate evaluation of the circulatory organ of the subject and/or an accurate diagnosis on the same can be made.

Here, preferably, the pulse wave analyzing means determines at least one of a maximum magnitude, a minimum magnitude, a rising point, a degree of sharpness % MAP, a maximum slope SLOPE of a rising portion, an area, an augmentation index AI, and a ratio of a maximum magnitude after change of posture of the subject to a maximum magnitude before the change of posture, of a heartbeat-synchronous pulse of the no-delay cuff volumetric pulse wave. Thus, the pulse wave analyzing means can accurately determine at least one of the blood pressure, the pulse wave propagation velocity, the arteriosclerosis evaluation index, and the autonomic nerve evaluation value of the subject.

According to a fifth aspect of the present invention, there is provided an apparatus for obtaining a pressure pulse wave, comprising a cuff adapted to be worn on a limb of a living subject so as to press an artery of the limb, a pressure sensor which is connected to the cuff, and which detects, as a cuff volumetric pulse wave, a pressure oscillation transmitted thereto from the cuff; an inverse transfer function memory which stores an inverse transfer function corresponding to a transfer function between intra-arterial pressure as input and pressure oscillation as output; and—a pressure pulse wave determining means for determining a pressure pulse wave produced in the artery, based on the cuff volumetric pulse wave detected by the pressure sensor the inverse transfer function stored by the inverse transfer function memory.

According to the fifth aspect of the present invention, the pressure pulse wave determining means determines, using the inverse transfer function, stored by the inverse transfer function memory, that corresponds to the pre-determined transfer function between input, i.e., pressure pulsation produced in the artery and output, i.e., pressure pulsation detected by the pressure sensor, the pressure pulse wave produced in the artery pressed by the cuff, based on the actual cuff volumetric pulse wave detected by the pressure sensor. Thus, the present apparatus can obtain the accurate cuff volumetric pulse wave that has substantially no distortion and enjoys high accuracy.

According to a sixth aspect of the present invention, there is provided an apparatus for analyzing a pressure pulse wave obtained from a living subject, comprising: the pressure pulse wave obtaining apparatus according to the fifth aspect of the present invention; and a pulse wave analyzing means for analyzing the pressure pulse wave produced in the artery, and obtained by the pressure pulse wave obtaining apparatus, and thereby determining at least one of a blood pressure, a pulse wave propagation velocity, an arteriosclerosis evaluation index, and an autonomic nerve evaluation value of the subject.

According to the sixth aspect of the present invention, the pulse wave analyzing means analyzes the pressure pulse wave obtained by the pressure pulse wave obtaining apparatus according to the fifth aspect of the invention, and thereby determines at least one of the blood pressure, the pulse wave propagation velocity, the arteriosclerosis evaluation index, and the autonomic nerve evaluation value of the subject. That is, at least one of the blood pressure, the pulse wave propagation velocity, the arteriosclerosis evaluation index, and the autonomic nerve evaluation value of the subject is determined by analyzing the accurate pressure pulse wave. Thus, an accurate evaluation of the circulatory organ of the subject and/or an accurate diagnosis on the same can be made.

According to a seventh aspect of the present invention, there is provided a method of obtaining a pressure pulse wave with an apparatus including a cuff adapted to be worn on a limb of a living subject so as to press an artery of the limb, a pressure sensor which is connected to the cuff, and which detects, as a cuff volumetric pulse wave, a pressure oscillation transmitted thereto from the cuff, an inverse transfer function memory which stores an inverse transfer function corresponding to a transfer function between intra-artery pressure as input and pressure oscillation as output, and a pressure pulse wave determining means for determining a pressure pulse wave produced in the artery, based on the cuff volumetric pulse wave detected by the pressure sensor and the inverse transfer function stored by the inverse transfer function memory, the method comprising: (a) a step of determining the inverse transfer function corresponding to the transfer function, and storing the determined inverse transfer function in the inverse transfer function memory, and (b) a step of determining, using the inverse transfer function stored by the inverse transfer function memory, the pressure pulse wave produced in the artery, based on the cuff volumetric pulse wave detected by the pressure sensor.

According to the seventh aspect of the present invention, after the inverse transfer function corresponding to the transfer function between input, i.e., pressure pulsation produced in the artery and output, i.e., pressure pulsation detected by the pressure sensor, is determined, and stored by the inverse transfer function memory, the pressure pulse wave produced in the artery is determined, using the inverse transfer function stored by the inverse transfer function memory, based on the actual pressure pulse wave detected by the pressure sensor. The thus determined pressure pulse wave has substantially no distortion and enjoys high accuracy.

According to an eighth aspect of the present invention, there is provided a method of obtaining a pressure pulse wave with an apparatus including a cuff adapted to be worn on a limb of a living subject so as to press an artery of the limb, a pressure sensor which is connected to the cuff, and which detects, as a cuff volumetric pulse wave, a pressure oscillation transmitted thereto from the cuff, an inverse transfer function memory which stores an inverse transfer function corresponding to a transfer function between intra-arterial pressure as input and pressure oscillation as output, a pressure pulse wave determining means for determining a pressure pulse wave produced in the artery, based on the cuff volumetric pulse wave detected by the pressure sensor and the inverse transfer function stored by the inverse transfer function memory, and a pulse wave analyzing means for analyzing the pressure pulse wave determined by the pressure pulse wave determining means, the method comprising: (a) a step of determining the inverse transfer function corresponding to the transfer function, and storing the determined inverse transfer function in the inverse transfer function memory, (b) a step of determining, using the inverse transfer function stored by the inverse transfer function memory, the pressure pulse wave produced in the artery, based on the cuff volumetric pulse wave detected by the pressure sensor, and (c) a step of analyzing the determined pressure pulse wave, and thereby determining at least one of a blood pressure, a pulse wave propagation velocity, an arteriosclerosis evaluation index, and an autonomic nerve evaluation value of the subject.

According to the eighth aspect of the present invention, after the inverse transfer function corresponding to the transfer function between input, i.e., pressure pulsation produced in the artery and output, i.e., pressure pulsation detected by the pressure sensor, is determined, and is stored by the inverse transfer function memory, the pressure pulse wave produced in the artery is determined, using the inverse transfer function stored by the inverse transfer function memory, based on the actual pressure pulse wave detected by the pressure sensor. The thus determined pressure pulse wave has substantially no distortion and enjoys high accuracy. In addition, the accurate pressure pulse wave is analyzed to determine at least one of the blood pressure, the pulse wave propagation velocity, the arteriosclerosis evaluation index, and the autonomic nerve evaluation value of the subject. Thus, the accurate cuff pressure pulse wave is analyzed and accordingly an accurate evaluation of the circulatory organ of the subject and/or an accurate diagnosis on the same can be made.

Here, preferably, the pulse wave analyzing means determines at least one of a maximum magnitude, a minimum magnitude, a rising point, a degree of sharpness % MAP, a maximum slope SLOPE of a rising portion, an area, an augmentation index AI, and a ratio of a maximum magnitude after change of posture of the subject to a maximum magnitude before the change of posture, of a heartbeat-synchronous pulse of the pressure pulse wave. Thus, the pulse wave analyzing means can accurately determine at least one of the blood pressure, the pulse wave propagation velocity, the arteriosclerosis evaluation index, and the autonomic nerve evaluation value of the subject.

BRIEF DESCRIPTION OF THE DRAWINGS

The above and optional objects, features, and advantages of the present invention will be better understood by reading the following detailed description of preferred embodiments of the invention when considered in conjunction with the drawings, in which.

DETAILED DESCRIPTION OF PREFERRED EMBODIMENTS

Hereinafter, there will be described a preferred embodiment of the present invention in detail by reference to the drawings.

Figure 1:
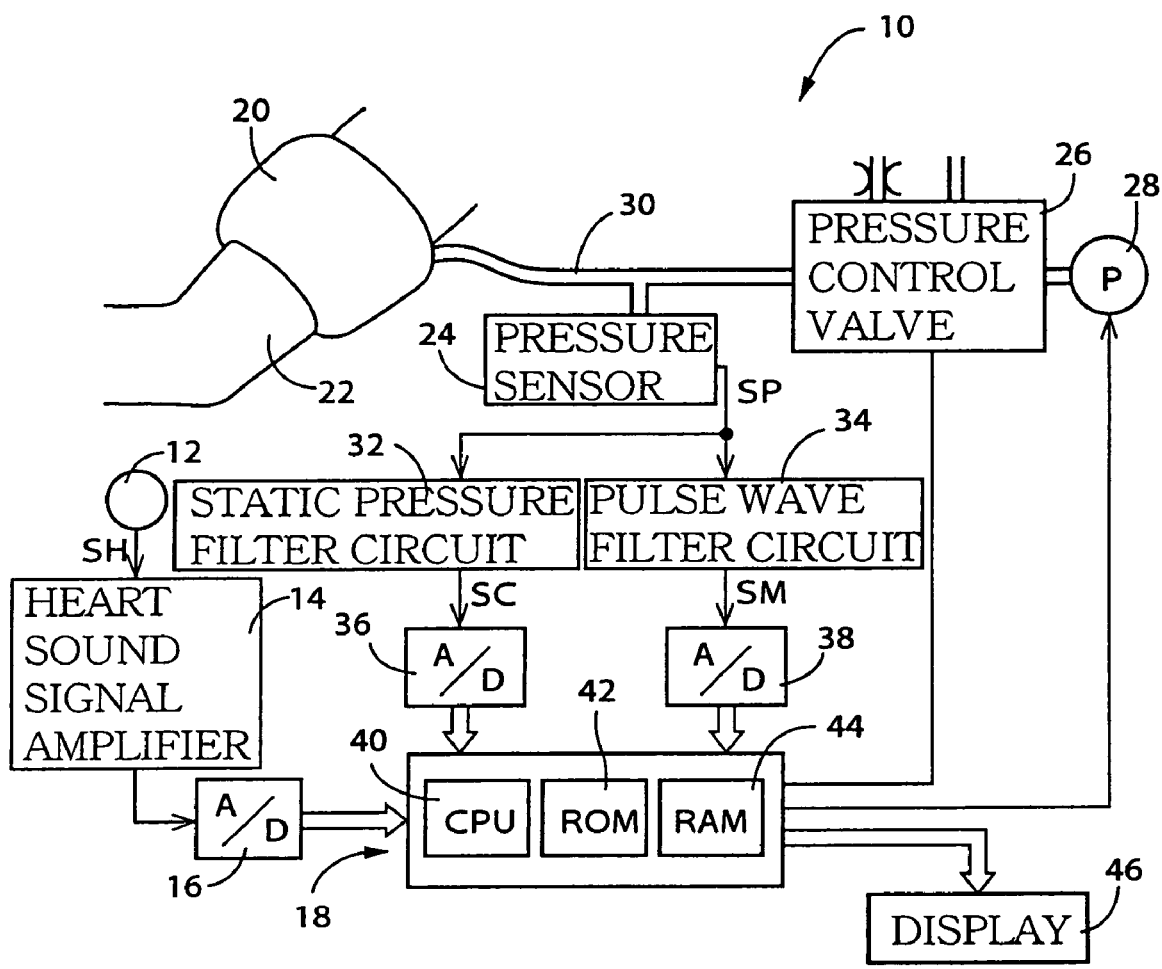
FIG. 1 is a diagrammatic view for explaining a construction of a subject-evaluation-value obtaining apparatus 10 functioning as a cuff volumetric pulse wave obtaining apparatus, a cuff volumetric pulse wave analyzing apparatus, a pressure pulse wave obtaining apparatus, and a pressure pulse wave analyzing apparatus to each of which the present invention is applied.

FIG. 1 is a diagrammatic view for explaining a construction of a subject-evaluation-value obtaining apparatus 10 functioning as a cuff volumetric pulse wave obtaining apparatus, a cuff volumetric pulse wave analyzing apparatus, a pressure pulse wave obtaining apparatus, and a pressure pulse wave analyzing apparatus to each of which the present invention is applied.

As shown in FIG. 1, the subject evaluation value measuring apparatus 10 includes a heart sound microphone 12 functioning as a second heartbeat synchronous signal detecting device that detects heart sounds as a second heartbeat synchronous signal that is produced in synchronism with a heartbeat of the subject. The heart-sound microphone 12 is attached, with, e.g., an adhesive tape, not shown, to a chest of a living subject, and incorporates a piezoelectric element, not shown, which converts the heart sounds produced from the heart of the subject, into an electric signal, i.e., a heart-sound signal SH representing a waveform of the heart sounds. A heart-sound-signal amplifier 14 incorporates four sorts of filters, not shown, which cooperate with each other to attenuate a low-pitch component of the heart sounds that has a great energy, so as to allow clear recording of a high-pitch component of the heart sounds. The heart-sound signal SH supplied from the heart-sound microphone 12 is amplified and filtered by the heart-sound-signal amplifier 14, and then is supplied to an electronic control device 18 via an A/D (analog-to-digital) converter 16.

The subject-evaluation-value measuring apparatus 10 additionally includes a cuff 20 which includes a belt-like cloth bag and a rubber bag accommodated in the cloth bag, and which is adapted to be worn on, e.g., a brachium 22 of a right arm of the subject. The cuff 20 is connected via a piping 30 to a pressure sensor 24, a pressure control valve 26, and an air pump 28. The piping 30 is provided by a flexible tube such as a rubber tube. The pressure control valve 26 is switchable to one of three positions, i.e., a pressure supply position in which the control valve 26 allows air pressure (i.e., pressurized air) to be supplied from the air pump 28 to the cuff 20; a slow deflation position in. which the control valve 26 slowly deflates the air pressure from the cuff 20; and a quick deflation position in which the control valve 26 quickly deflates the air pressure from the cuff 20.

The pressure sensor 24 detects an air pressure $P_K$ in the cuff 20, and supplies a pressure signal SP representing the detected air pressure $P_K$, to each of a static-pressure filter circuit 32 and a pulse-wave filter circuit 34. The static-pressure filter circuit 32 includes a low-pass filter which extracts, from the pressure signal SP, a cuff pressure signal SC representing a static component of the detected air pressure, i.e., a pressing pressure of the cuff 20. The filter circuit 32 supplies the cuff pressure signal SC to the electronic control device 18 via an A/D converter 36. The pulse-wave filter circuit 34 includes a band-pass filter which extracts, from the pressure signal SP representing the cuff pressure $P_K$, a cuff pulse wave signal SM representing an oscillatory or alternating-current (i.e., periodic-pulsation) component of the detected air pressure. The filter circuit 34 supplies the cuff pulse wave signal SM to the electronic control device 18 via an A/D converter 38. The cuff pulse wave signal SM represents a cuff pulse wave (i.e., a brachial-artery pulse wave) BW, i.e., a pressure oscillation that is periodically produced from an artery of the brachium 22 in synchronism with a heartbeat of the subject. The pressure sensor 24 and the pulse-wave filter circuit 34 cooperate with each other to function as a cuff pulse wave detecting device, a first pulse wave detecting device, or a first heartbeat-synchronous signal detecting device that detects the cuff pulse wave BW as a first heartbeat-synchronous signal that is produced in synchronism with a heartbeat of the subject.

The electronic control device 28 is provided by a so-called microcomputer including a CPU (central processing unit) 40, a ROM (read only memory) 42, a RAM (random access memory) 44, and an I/O (input-and-output) port, not shown. The CPU 40 processes signals according to control programs pre-stored in the ROM 42, while utilizing a temporary-storage function of the RAM 44. The CPU 40 outputs, from the I/O port, drive signals to the pressure control valve 26 and the air pump 28, so as to carry out a blood pressure measurement and a pulse wave measurement. More specifically described, in a blood pressure measurement mode, the CPU 40 operates the pressure control valve 26 and the air pump 28, so as to increase the pressing pressure of the cuff 20 (i.e., the cuff pressure) up to, e.g., 180 mmHg that would be higher than a systolic blood pressure of the brachium 22 of the subject, subsequently slowly decrease the cuff pressure, and quickly decrease the cuff pressure after completion of blood pressure measurement. In a pulse wave detection mode, the CPU 40 operates the pressure control valve 26 and the air pump 28, so as to increase the cuff pressure up to a prescribed pulse wave detection pressure, e.g., 60 mmHg that would be sufficiently lower than a diastolic blood pressure of the brachium 22 but assure that the cuff pulse wave signal SM supplied from the pulse wave filter circuit 34 has a sufficiently great magnitude. In addition, the CPU 40 processes the signals supplied to the electronic control device 18, so as to determine a cuff volumetric pulse wave and an intra-arterial pressure pulse wave each of which has no time delay, and obtain pulse wave propagation velocity-related information, and operates a display device 46, such as a CRT (cathode ray tube) or an LCD (liquid crystal display), to display the thus obtained information.

Figure 2:
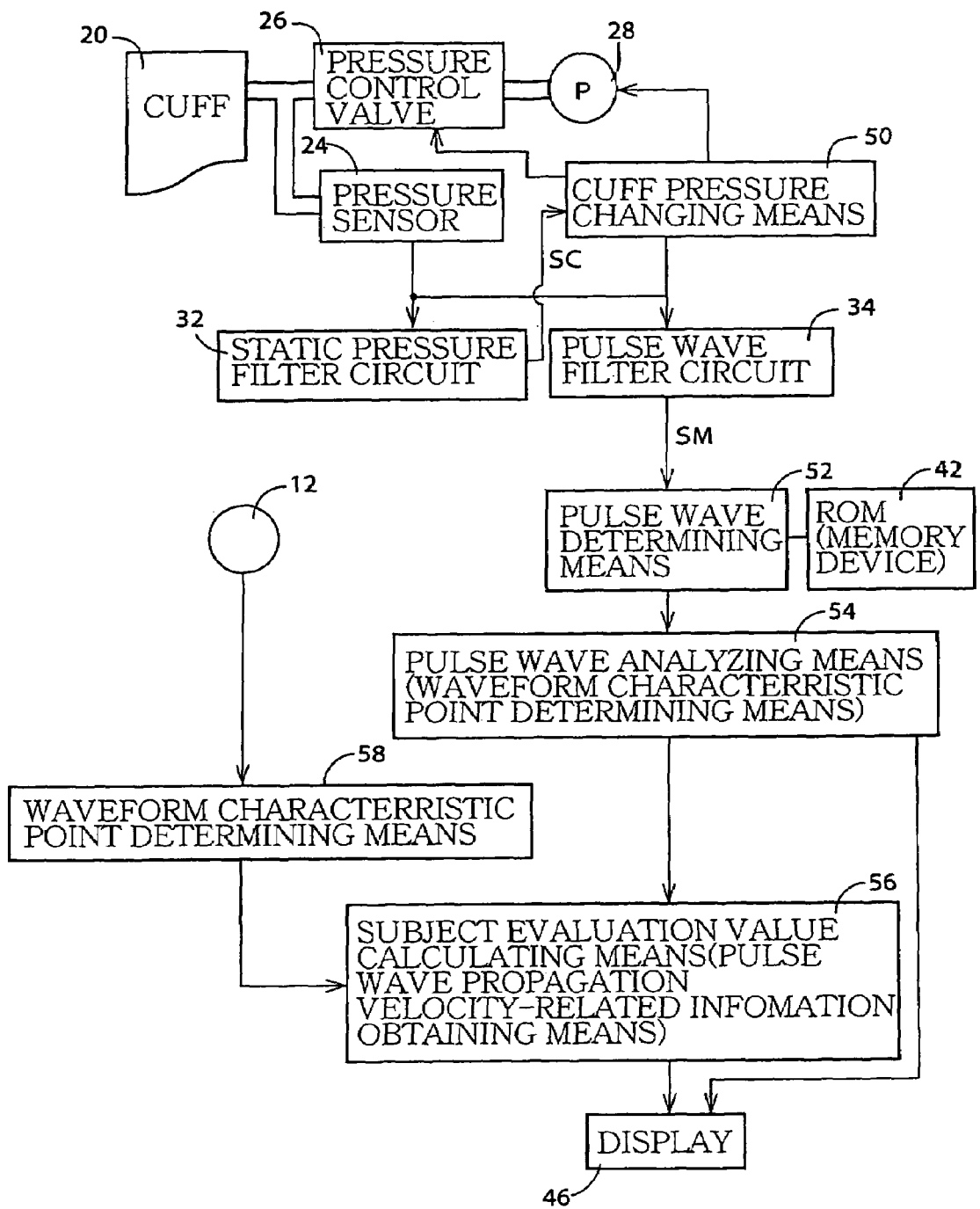
FIG. 2 is a diagrammatic view for explaining essential control functions of an electronic control device of the apparatus shown in FIG. 1.

FIG. 2 is a diagrammatic view for explaining essential control functions of the electronic control device 18 of the present measuring apparatus 10. A cuff-pressure changing device or means 50 reads the pressing pressure of the cuff 20 (i.e., the cuff pressure) represented by the cuff pressure signal SC supplied from the static-pressure filter circuit 32, and controls the pressure control valve 26 and the air pump 28. More specifically described, during a blood pressure measurement using the cuff 20, the changing means 50 operates the valve 26 and the pump 28 so as to increase the cuff pressure up to, e.g., 180 mmHg that would be higher than a systolic blood pressure of the brachium 22, subsequently slowly decrease the cuff pressure, and then quickly decrease the cuff pressure after completion of the blood pressure measurement. During a pulse wave detection for obtaining pulse wave propagation velocity-related information, the CPU 40 operates the valve 26 and the pump 28, so as to increase and keep the cuff pressure to and at a prescribed pulse wave detection pressure, e.g., 60 mmHg.

The ROM 42, functioning as a memory device, stores, in advance, a transfer function H(f) that defines a transfer of a cuff volumetric pulse wave $P_K(t)$ that is pressure oscillation produced in the cuff 12 and has no transfer delay (hereinafter, referred to as the "no-delay cuff volumetric pulse wave $P_K(t)$"), or a pressure pulse wave $P_{BP}(t)$ that is pressure pulsation produced in the artery pressed by the cuff 20, to the cuff pulse wave signal SM representing the pressure oscillation detected by the pressure sensor 24; and additionally stores an inverse transfer function 1 H(f). Providing that the no-delay cuff volumetric pulse wave as the pressure oscillation produced in the cuff 20, or the pressure pulse wave as the pressure pulsation produced in the artery pressed by the cuff 20 are expressed as $x_1(t)$ and $x_2(t)$, respectively, and the cuff pulse wave signal SM detected and outputted by the pressure sensor 24 is expressed as y(t), the above-indicated transfer function H(f) is expressed as the ratio (=Y(f)/X(f)) of frequency function Y(f) to frequency function X(f), according to the following expression (1), where the frequency functions X(f), Y(f) are obtained by subjecting, to Fourier transform, time function $x_1(t)$ or $x_2(t)$ and time function y(t), respectively:

$$H(f)=Y(f)/X(f) \qquad \text{Expression (1)}$$

Generally, the transfer function H(f) is expressed as a complex number and polar coordinates, according to the following expression (2), where|H(f)| is gain of transfer function H(f); andφ is phase:

$$H(f)=|H(f)|\exp(j\ \phi(f)) \qquad \text{Expression (2)}$$

However, for convenience, power spectrum (i.e., frequency analysis spectrum) $S_{xx}(f)$ of input signal x(t), and cross power spectrum $S_{xy}(f)$ between input signal $x_1(t)$ or $x_2(t)$ and output signal y(t) may be calculated, and transfer function H(f) may be determined based on the power spectrum $S_{xx}(f)$ and the cross power spectrum $S_{xy}(f)$, according to the following expression (3):

$$H(f)=S_{xx}(f)/S_{xy}(f) \qquad \text{Expression (3)}$$

Figure 3:
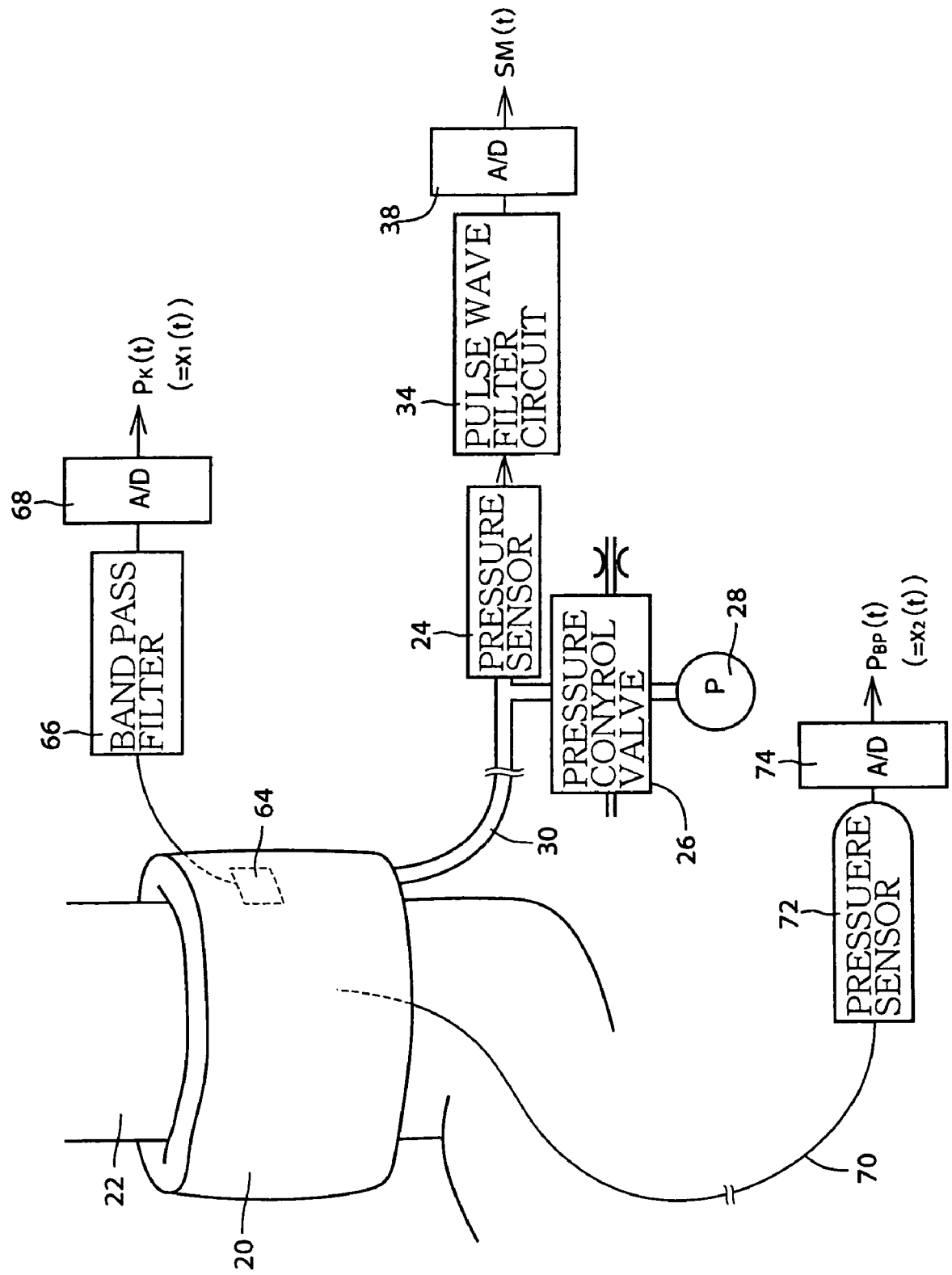
FIG. 3 is a view for explaining a method of determining a transfer function H(f) or G(s)

FIG. 3 shows an apparatus for carrying out a method of obtaining the above-indicated transfer function H(f). A pressure sensor 64, provided in the cuff 20, directly detects an air pressure in the cuff 20, and outputs a non-delay cuff volumetric pulse wave $P_K(t)$ via a band-pass filter 66 and an A/D converter 68. In addition, a pressure sensor 72, connected to a catheter 70, directly detects blood pressure in an artery pressed by the cuff 20, and outputs a pressure pulse wave $P_{BP}(t)$ via an A/D. converter 74 Subsequently, a power spectrum (frequency analysis spectrum) $S_{xx}(f)$ of the cuff volumetric pulse wave $P_K(t)$ or the pressure pulse wave $P_{BP}(t)$, each thus obtained, is calculated, and additionally a cross power spectrum $S_{xy}(f)$ between input signal $P_K(t)$ or $P_{BP}(t)$ and output signal, i.e., cuff pulse wave SM(t) is calculated. Finally, the transfer function H(f) is determined based on the spectrums $S_{xx}(f)$, $S_{xy}(f)$ according to the above-indicated expression (3), and its inverse transfer function 1/H(f) is calculated. The thus obtained functions H(f), 1/H(f) are stored, in advance, in the ROM 42. Those functions H(f), 1/H(f) may be commonly used for a plurality of living subjects. Alternatively, functions H(f), 1/H(f) specific to each individual subject may be obtained from the each subject, before measurement.

Back to FIG. 2, a pulse wave determining device or means 52 uses the transfer function H(f) and the inverse transfer function 1/H(f), pre-stored in the ROM 42, and determines a cuff volumetric pulse wave $P_K(t)$ or a pressure pulse wave $P_{BP}(t)$ that is free of time delay or distortion, based on the cuff pulse wave signal SM(t) that is actually obtained from the subject. For example, first, frequency function X(f) is calculated, according to a modified expression, X(f)=Y(f)/H(f), derived from the expression (1), based on frequency function Y(f) obtained by subjecting the cuff pulse wave signal SM(t) to Fourier transform. Then, when the frequency function X(f) is subjected to inverse Fourier transform, a cuff volumetric pulse wave $P_K(t)$ or a pressure pulse wave $P_{BP}(t)$, each free of time delay or distortion, is determined (i.e., estimated). Thus, the pulse wave determining means 52 functions as a cuff volumetric pulse wave determining means or a pressure pulse wave determining means.

A pulse wave analyzing device or means 54 analyzes the cuff volumetric pulse wave $P_K(t)$ or the pressure pulse wave $P_{BP}(t)$, each free of time delay or distortion, determined by the pulse wave determining means 52, and calculates a waveform characteristic value corresponding to the purpose of analysis. For example, the analyzing means 54 calculates, for determining any one of a blood pressure, a pulse wave propagation velocity, an arteriosclerosis evaluation index, and an autonomic nerve evaluation value of the subject, at least one of waveform characteristic values including a maximum magnitude and/or a minimum magnitude, a rising point, a dicrotic notch, an area ratio, an amplitude, a sharpness % MAP, a maximum slope SLOPE of a rising portion, a pulse area, an augmentation index, and ratio of a maximum magnitude after change of posture to a maximum magnitude before the change of posture, of the cuff volumetric pulse wave $P_K(t)$ or the pressure pulse wave $P_{BP}(t)$. The analyzing means 54 operates the display device 46 to display the thus calculated waveform characteristic value or values.

For example, a maximum magnitude and/or a minimum magnitude of a heartbeat-synchronous pulse of the cuff volumetric pulse wave $P_K(t)$ or the pressure pulse wave $P_{BP}(t)$ is or are determined for iteratively estimating systolic and/or diastolic blood pressure of the subject according to a pre-stored relationship between blood pressure and pulse-wave magnitude; a rising point or a dicrotic notch of a pulse of the pulse wave $P_K(t)$, $P_{BP}(t)$ is determined, with respect to each of two pulse waves detected from two body portions of the subject, as a waveform characteristic point (i.e., a time-measurement reference point) for iteratively estimating a pulse wave propagation velocity PWV at which the pulse wave propagates between the two body portions, according to a pre-stored relationship between pulse wave propagation velocity PWV (i.e., a sort of pulse wave propagation velocity-related information corresponding to arteriosclerosis) and time difference between two body portions; an area ratio VR of a pulse of the pulse wave $P_K(t)$, $P_{BP}(t)$ is determined for iteratively calculating an estimated blood pressure EBP according to a pre-stored relationship between estimated blood pressure EBP, and pulse wave propagation velocity PWV, area ratio VR, and pulse period RR; the area ratio VR is also used for evaluating a cardiac output of the subject; an amplitude, a maximum slope SLOPE of a rising portion, a sharpness % MAP as the ratio of height position of gravity center of pulse area to pulse amplitude, a rising-portion percentage value as the ratio of rising-portion time to pulse period, and a peak index value PI as the ratio of interval between greatest peak and next peak, to pulse period, of a pulse of the pulse wave $P_K(t)$, $P_{BP}(t)$, is determined for iteratively calculating an estimated blood pressure according to a pre-stored relationship between estimated blood pressure and waveform characteristic value; an augmentation index AI as the ratio of difference $\Delta PP$ ($=A_2-A_1$) between pulse magnitude $A_1$ corresponding to maximum point of incident wave component and pulse magnitude $A_2$ corresponding to maximum point of reflected wave component, to maximum amplitude $A_{max}$, of a pulse of the pulse wave $P_K(t)$, $P_{BP}(t)$, is determined for determining a degree of arteriosclerosis according to a pre-stored relationship between degree of arteriosclerosis and augmentation index AI; a ratio of a maximum magnitude after change of posture of the subject, to a maximum magnitude before the change of posture, of a pulse of the pulse wave $P_K(t)$, $P_{BP}(t)$ is determined for iteratively calculating a blood pressure recovery ratio corresponding to autonomic imbalance; and a maximum magnitude of a pulse of the pulse wave $P_K(t)$, $P_{BP}(t)$ is determined for obtaining fluctuations of maximum magnitude that correspond to the activity of autonomic nerve of the subject.

A subject evaluation value calculating device or means 56 calculates a blood pressure value, an arteriosclerosis evaluation value, an autonomic nerve evaluation value, etc. of the subject, based on one or more waveform characteristic values of the cuff volumetric pulse wave $P_K(t)$ or the pressure pulse wave $P_{BP}(t)$, determined by the pulse wave analyzing means 54, and operates the display device 46 to display the thus calculated subject evaluation value or values.

In the present embodiment, the pulse wave analyzing means 54. determines the rising point or dicrotic notch. of the cuff volumetric pulse wave $P_K(t)$ or the pressure pulse wave $P_{BP}(t)$, as a waveform characteristic point (i.e., a time-measurement reference point) of a pulse wave detected from the brachium 22, where the cuff 20 is worn, as one of two body portions of the subject, so that the subject evaluation value calculating means 56 uses the rising point or dicrotic notch thus determined, for iteratively estimating a pulse wave propagation velocity PWV (i.e., a sort of pulse wave propagation velocity-related information) at which the pulse wave propagates between the two body portions, according to a pre-stored relationship between pulse wave propagation velocity PWV and time difference between two body portions. Thus, the pulse wave analyzing device or means 54 also functions as a (first) waveform characteristic point determining device or means; and the subject evaluation value calculating device or means 56 also functions as a pulse wave propagation velocity-related information obtaining device or means.

Figure 4:
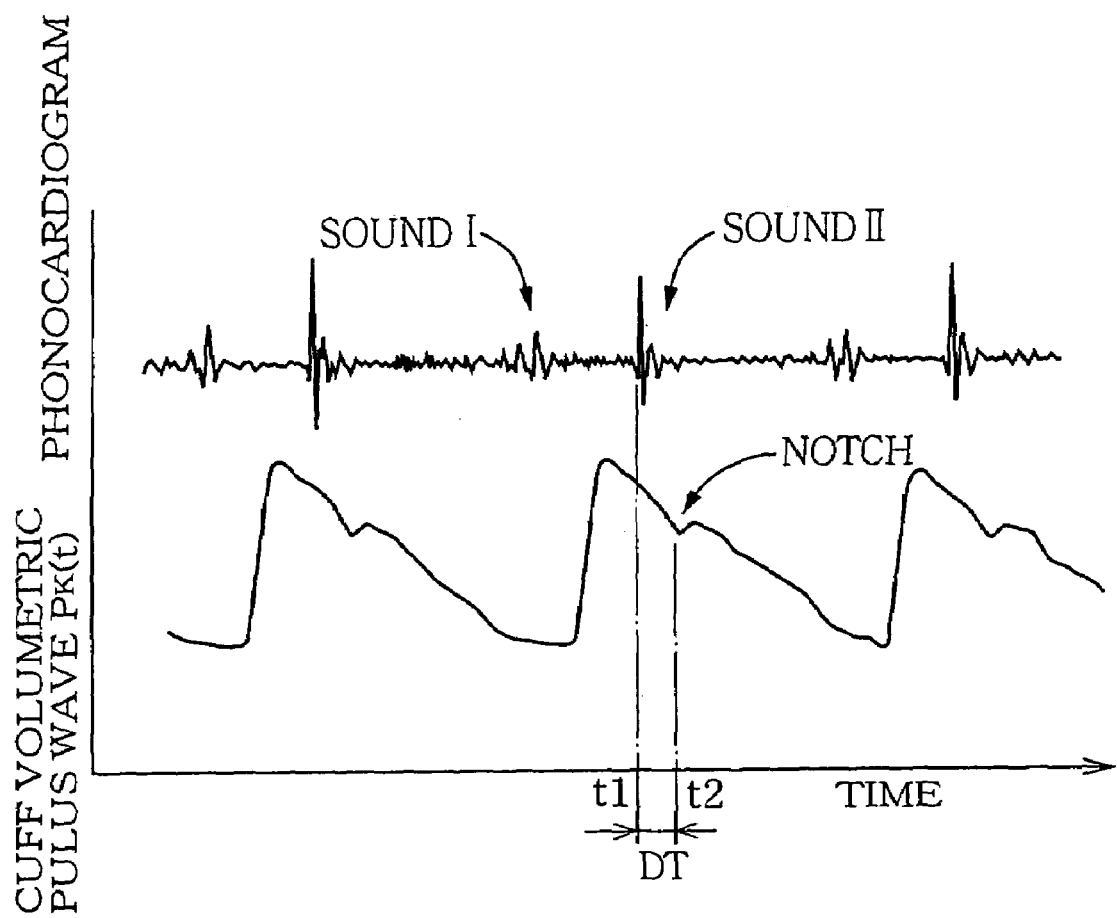
FIG. 4 is a time chart for explaining a time difference that is calculated by a subject-evaluation-value calculating means shown in FIG. 2.

A (second) waveform characteristic point determining device or means 58 determines, on the heart-sound waveform represented by the heart sound signal SH supplied from the heart sound microphone 12, a start point of a heart sound II corresponding to the dicrotic notch of the brachial-artery pulse wave BW. As shown in FIG. 4, the subject evaluation value calculating means 56 calculates, as a pulse wave propagation time DT, a time difference between a time of detection of the start point of heart sound II, determined by the second waveform characteristic point determining means 58, and a time of detection of the waveform characteristic point (e.g., the notch) of the cuff volumetric pulse wave $P_K(t)$ or the pressure pulse wave $P_{BP}(t)$, determined by the pulse wave analyzing means 54, i.e., the first waveform characteristic point determining means. Optionally, the subject evaluation value calculating means 56 additionally calculates a pulse wave propagation velocity PWV of the subject, based on the thus calculated pulse wave propagation time DT, according to the following expression (4), where L indicates a distance from the subject's heart to the brachium 22 where the cuff 20 is worn, and is replaced with a constant value that is experimentally determined, in advance:

$$PWV=L/DT \quad \text{Expression (4)}$$

Finally, the calculating means 56 operates the display device 46 to display the thus calculated pulse wave propagation time DT or pulse wave propagation velocity PWV.

Figure 5:
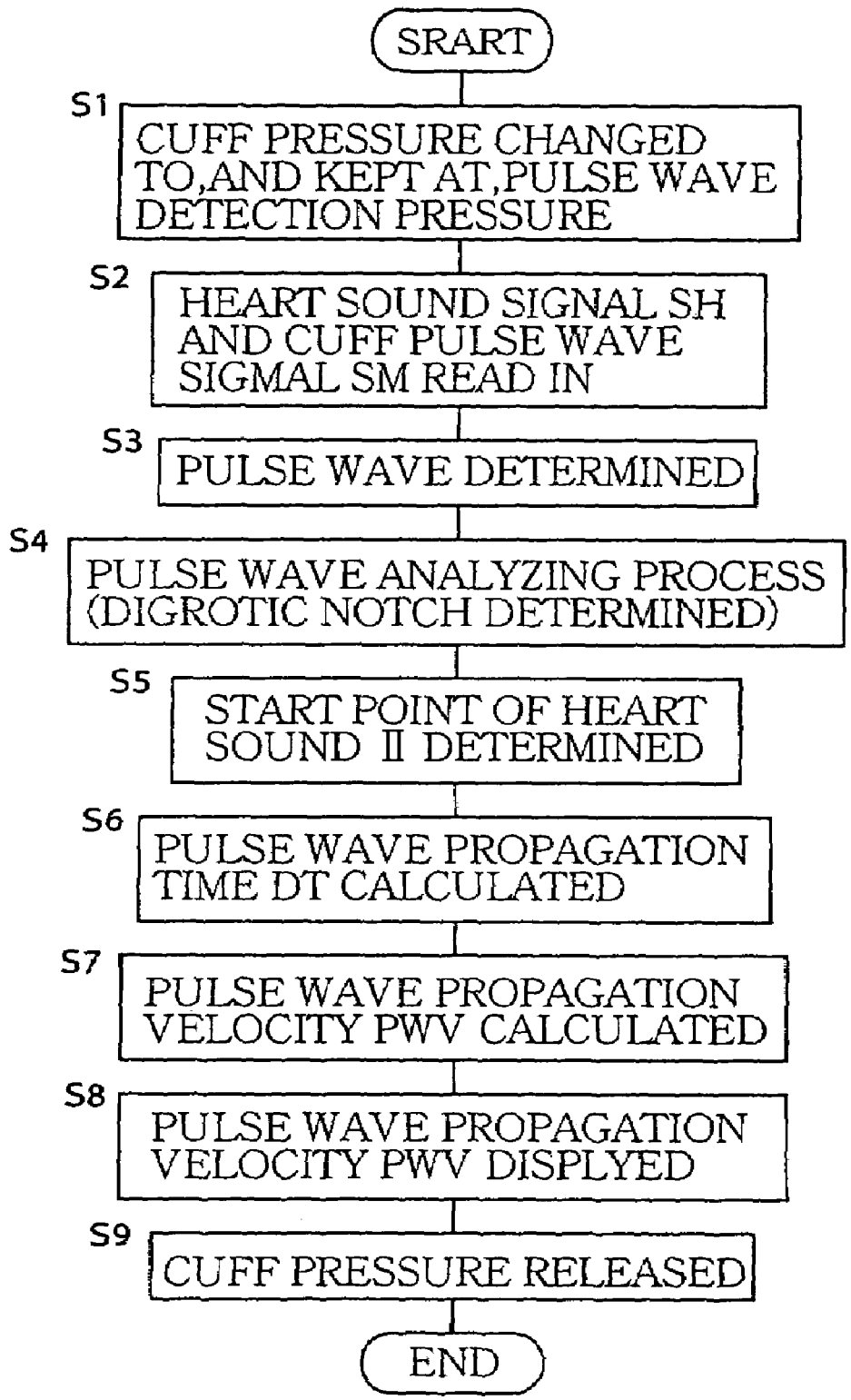
FIG. 5 is a flow chart representing the essential control functions of the electronic control device shown in FIG. 1.

FIG. 5 is a flow chart for explaining the essential control functions of the electronic control device 18, shown in FIG. 2.

First, at Step S1 corresponding to the cuff pressure changing means 50, the control device 18 controls the pressure control valve 26 and the air pump 28 to change and keep the pressing pressure of the cuff 20 (i.e., the cuff pressure) to and at the prescribed pulse wave detection pressure. Subsequently, at Step S2, in a state in which the cuff pressure is kept at the pulse wave detection pressure, the control device 18 reads in, at a prescribed sampling period, respective lengths of the heart sound signal SH and the cuff pulse wave signal SM, for a prescribed time duration corresponding to at least one heartbeat of the subject.

Then, the control of the control device 18 proceeds with Step S3 corresponding to the pulse wave determining means 5 functioning as the cuff volumetric pulse wave determining means or the pressure pulse wave determining means. At Step S3, the control device 18 determines, using the transfer function H(f) or the inverse transfer function 1/H(f) pre-stored in the ROM 42, a cuff volumetric pulse wave $P_K(t)$ that has substantially no time delay or distortion, or a pressure pulse wave $P_{BP}(t)$ produced in the brachial artery, based on the length of actual cuff pulse wave signal SM read in at Step S2. For example, using the expression, X(f)=Y(f)/H(f), derived from the above-indicated expression (1), a frequency function X(f) is calculated based on a frequency function Y(f) obtained by subjecting the cuff pulse wave signal SM to Fourier transform, and the thus obtained frequency function X(f) is subjected to inverse Fourier transform, to determine or estimate a cuff volumetric pulse wave $P_K(t)$ that has a cuff volumetric pulse wave $P_K(t)$ that is produced in the cuff 20 and has substantially no time delay or distortion, or a pressure pulse wave $P_{BP}(t)$ that is produced in the brachial artery pressed by the cuff 20.

Then, the control goes to Step S4 corresponding to the pulse wave analyzing means 54 functioning as the (first)

waveform characteristic point determining means. At Step S4, the control device 18 analyzes the cuff volumetric pulse wave $P_K(t)$, determined at Step S3, that is produced in the cuff 20 and has substantially no time delay or distortion, or the pressure pulse wave $P_{BP}(t)$, also determined at Step S3, that is produced in the brachial artery pressed by the cuff 20, and determines one or more waveform characteristic points corresponding to analysis purposes, e.g., a dicrotic notch as a reference point to calculate a pulse wave propagation velocity, and a time, t2, (FIG. 4) of detection of the determined dicrotic notch. Subsequently, the control goes to Step S5 corresponding to the (second) waveform characteristic point determining means 58. At Step S5, the control device 18 determines a start point of a heart sound II (FIG. 4) detected from the subject. For example, the control device 18 squares an amplitude of the heart sound signal SH, read in at Step S2, with respect to a base line (i.e., a level corresponding to no heart sounds), and determines, as a time, t1, of detection of the start point of heart sound II, a point where the amplitude of the thus squared signal or waveform exceeds a prescribed threshold value TH.

Subsequently, the control goes to Steps S6 and S7 corresponding to the subject evaluation value calculating means 56 functioning as the pulse wave propagation velocity determining means. First, at Step S6, the control device 18 determines, as a pulse wave propagation velocity DT, a time difference between the time t1 of detection of the start point of heart sound II, determined at Step S5, and the time t2 of detection of dicrotic notch, determined at Step S4; and, at Step S7, the control device 18 determines a pulse wave propagation velocity PWV by replacing the above-indicated expression (4) with the pulse wave propagation time DT determined at Step S6. Then, at Step S8, the control device 18 operates the display device 46 to display the pulse wave propagation velocity PWV determined at Step S7 and, at Step S9, the control device 18 operates the pressure control valve 26 to deflate the cuff 20. Thus, this routine is finished.

As is apparent from the foregoing description, in the subject evaluation value measuring apparatus 10 functioning as the cuff volumetric pulse wave obtaining apparatus, the pulse wave determining means (the cuff volumetric pulse wave determining means) 52 determines, using the inverse transfer function 1/H(f), stored by the ROM (the inverse transfer function memory) 42, that corresponds to the predetermined transfer function H(f) between input, i.e., pressure pulsation produced in the cuff 20 and output, i.e., pressure pulsation detected by the pressure sensor 24, the no-delay, initial cuff volumetric pulse wave $P_K(t)$, based on the actual cuff pulse wave signal SM detected by the pressure sensor 24. The thus determined cuff volumetric pulse wave $P_K(t)$ has substantially no distortion and accordingly enjoys high accuracy.

In addition, in the subject evaluation value measuring apparatus 10 functioning as the cuff volumetric pulse wave analyzing apparatus, the pulse wave analyzing means 54 analyzes the no-delay cuff volumetric pulse wave $P_K(t)$ determined by the pulse wave determining means (the cuff volumetric pulse wave determining means) 52 of the above indicated cuff volumetric pulse wave obtaining apparatus, and thereby determines at least one of the blood pressure, the pulse wave propagation velocity, the arteriosclerosis evaluation index, and the autonomic nerve evaluation value of the subject. That is, at least one of the blood pressure, the pulse wave propagation velocity, the arteriosclerosis evaluation index, and the autonomic nerve evaluation value of the subject is determined by analyzing the accurate cuff volumetric pulse wave $P_K(t)$. Thus, an accurate evaluation of the circulatory organ of the subject or an accurate diagnosis on the same can be made.

In addition, the subject evaluation value measuring apparatus 10 functioning as the cuff volumetric pulse wave obtaining apparatus, is used for carrying out the method of obtaining the cuff volumetric pulse wave from the subject, the method including (a) the step of determining the inverse transfer function 1/H(f) corresponding to the transfer function H(f) between input, i.e., pressure pulsation produced in the cuff 20 and output, i.e., pressure pulsation detected by the pressure sensor 24, and storing the determined inverse transfer function 1/H(f) in the ROM (the inverse transfer function memory) 42, and (b) the step of determining, using the inverse transfer function 1/H(f) stored by the ROM 42, the no-delay cuff volumetric pulse wave $P_K(t)$, based on the actual cuff pulse wave signal SM detected by the pressure sensor 24. The measuring apparatus 10 includes the pressure sensor 24 which is connected to the cuff 20 worn on the limb 22 of the subject so that the pressure pulsation is produced in the cuff 20, and which detects, as the actual cuff pulse wave signal SM, the pressure oscillation transmitted thereto from the cuff 20; the ROM 42 that stores the inverse transfer function 1/H(f) corresponding to the transfer function H(f) between input, i.e., pressure pulsation produced in the cuff 20 and output, i.e., pressure oscillation detected by the pressure sensor 24; and the pulse wave determining means (the cuff volumetric pulse wave determining means) 52 that determines, using the inverse transfer function 1/H(f) stored by the ROM 42, the no-delay cuff volumetric pulse wave $P_K(t)$, based on the actual cuff pulse wave signal SM detected by the pressure sensor 24. The thus determined cuff volumetric pulse wave $P_K(t)$ has substantially no distortion and accordingly enjoys high accuracy.

In addition, the subject evaluation value measuring apparatus 10 functioning as the cuff volumetric pulse wave analyzing apparatus, is used for carrying out the method of obtaining the cuff volumetric pulse wave from the subject, the method including (a) the step of determining the inverse transfer function 1/H(f) corresponding to the transfer function H(f) between input, i.e., pressure pulsation produced in the cuff 20 and output, i.e., pressure pulsation detected by the pressure sensor 24, and storing the determined inverse transfer function 1/H(f) in the ROM (the inverse transfer function memory) 42, (b) the step of determining, using the inverse transfer function 1/H(f) stored by the ROM 42, the no-delay cuff volumetric pulse wave $P_K(t)$, based on the actual cuff pulse wave signal SM detected by the pressure sensor 24, and (c) the step of analyzing the thus determined no-delay cuff volumetric pulse wave, and thereby determining at least one of the blood pressure, the pulse wave propagation velocity, the arteriosclerosis evaluation index, and the autonomic nerve evaluation value of the subject. The measuring apparatus 10 includes the pressure sensor 24 which is connected to the cuff 20 worn on the limb 22 of the subject so that the pressure pulsation is produced in the cuff 20, and which detects, as the actual cuff pulse wave signal SM, the pressure oscillation transmitted thereto from the cuff 20; the ROM 42 that stores the inverse transfer function 1/H(f) corresponding to the transfer function H(f) between input, i.e., pressure pulsation produced in the cuff 20 and output, i.e., pressure oscillation detected by the pressure sensor 24; the pulse wave determining means (the cuff volumetric pulse wave determining means) 52 that determines, using the inverse transfer function 1/H(f) stored by the ROM 42, the no-delay cuff volumetric pulse wave $P_K(t)$, based on the actual cuff pulse wave signal SM detected by the pressure sensor 24; and the pulse wave analyzing means (the waveform characteristic point determining means) 54 that analyzes the no-delay cuff volumetric pulse wave $P_K(t)$ determined by the pulse wave determining means 52. Thus, the accurate cuff volumetric pulse wave $P_K(t)$ is analyzed and accordingly an accurate evaluation of the circulatory organ of the subject or an accurate diagnosis on the same can be made.

In each of the illustrated embodiments, the pulse wave analyzing means 54 determines at least one of the maximum magnitude, the minimum magnitude, the rising point, the degree of sharpness % MAP, the maximum slope SLOPE of the rising portion, the pulse area, the augmentation index AI, and the ratio of maximum magnitude after change of posture of the subject to maximum magnitude before the change of posture, of heartbeat-synchronous pulse of the no-delay cuff volumetric pulse wave $P_K(t)$ determined by the pulse wave determining means 52. Thus, the pulse wave analyzing means 54 can accurately determine at least one of the blood pressure, the pulse wave propagation velocity, the arteriosclerosis evaluation index, and the autonomic nerve evaluation value of the subject.

In addition, in the subject evaluation value measuring apparatus 10 functioning as the pressure pulse wave obtaining apparatus, the pulse wave determining means (the pressure pulse wave determining means) 52 determines, using the inverse transfer function 1/H(f), stored by the ROM (the inverse transfer function memory) 42, that corresponds to the pre-determined transfer function H(f) between input, i.e., pressure pulsation produced in the cuff 20 and output, i.e., pressure pulsation detected by the pressure sensor 24, the no-delay pressure pulse wave $P_{BP}(t)$, based on the actual cuff pulse wave signal SM detected by the pressure sensor 24. The thus determined pressure pulse wave $P_{BP}(t)$ has substantially no distortion and enjoys high accuracy.

In addition, in the subject evaluation value measuring apparatus 10 functioning as the pressure pulse wave analyzing apparatus, the pulse wave analyzing means 54 analyzes the no-delay pressure pulse wave $P_{PB}(t)$ determined by the pulse wave determining means (the pressure pulse wave determining means) 52 of the above indicated pressure pulse wave obtaining apparatus, and thereby determines at least one of the blood pressure, the pulse wave propagation velocity, the arteriosclerosis evaluation index, and the autonomic nerve evaluation value of the subject. That is, at least one of the blood pressure, the pulse wave propagation velocity, the arteriosclerosis evaluation index, and the autonomic nerve evaluation value of the subject is determined by analyzing the accurate pressure pulse wave $P_{PB}(t)$. Thus, an accurate evaluation of the circulatory organ of the subject or an accurate diagnosis on the same can be made.

In addition, the subject evaluation value measuring apparatus 10 functioning as the pressure pulse wave obtaining apparatus, is used for carrying out the method of obtaining the pressure pulse wave from the subject, the method including (a) the step of determining the inverse transfer function 1/H(f) corresponding to the transfer function H(f) between input, i.e., pressure pulsation produced in the cuff 20 and output, i.e., pressure pulsation detected by the pressure sensor 24, and storing the determined inverse transfer function 1/H(f) in the ROM (the inverse transfer function memory) 42, and (b) the step of determining, using the inverse transfer function 1/H(f) stored by the ROM 42, the pressure pulse wave $P_{BP}(t)$ produced in the artery pressed by the cuff 20, based on the actual cuff pulse wave signal SM detected by the pressure sensor 24. The measuring apparatus 10 includes the pressure sensor 24 which is connected to the cuff 20 worn on the limb 22 of the subject so that the pressure pulsation is produced in the cuff 20, and which detects, as the actual cuff pulse wave signal SM, the pressure oscillation transmitted thereto from the cuff 20; the ROM 42 that stores the inverse transfer function 1/H(f) corresponding to the transfer function H(f) between input, i.e., pressure pulsation produced in the cuff 20 and output, i.e., pressure oscillation detected by the pressure sensor 24; and the pulse wave determining means (the pressure pulse wave determining means) 52 that determines, using the inverse transfer function 1/H(f) stored by the ROM 42, the pressure pulse wave $P_{BP}(t)$ produced in the artery pressed by the cuff 20, based on the actual cuff pulse wave signal SM detected by the pressure sensor 24. The thus determined pressure pulse wave $P_{BP}(t)$ has substantially no distortion and enjoys high accuracy.

In addition, the subject evaluation value measuring apparatus 10 functioning as the pressure pulse wave analyzing apparatus, is used for carrying out the method of obtaining the pressure pulse wave from the subject, the method including (a) the step of determining the inverse transfer function 1/H(f) corresponding to the transfer function H(f) between input, i.e., pressure pulsation produced in the cuff 20 and output, i.e., pressure pulsation detected by the pressure sensor 24, and storing the determined inverse transfer function 1/H(F) in the ROM (the inverse transfer function memory) 42, (b) the step of determining, using the inverse transfer function 1/H(f) stored by the ROM 42, the pressure pulse wave $P_{BP}(t)$ produced in the artery pressed by the cuff 20, based on the actual cuff pulse wave signal SM detected by the pressure sensor 24, and (c) the step of analyzing the thus determined pressure pulse wave $P_{BP}(t)$ produced in the artery, and thereby determining at least one of the blood pressure, the pulse wave propagation velocity, the arteriosclerosis evaluation index, and the autonomic nerve evaluation value of the subject. The measuring apparatus 10 includes the pressure sensor 24 which is connected to the cuff 20 worn on the limb 22 of the subject so that the pressure pulsation is produced in the cuff 20, and which detects, as the actual cuff pulse wave signal SM, the pressure oscillation transmitted thereto from the cuff 20; the ROM 42 that stores the inverse transfer function 1/H(f) corresponding to the transfer function H(f) between input, i.e., pressure pulsation produced in the cuff 20 and output, i.e., pressure oscillation detected by the pressure sensor 24; the pulse wave determining means (the pressure pulse wave determining means) 52 that determines, using the inverse transfer function 1/H(f) stored by the ROM 42, the pressure pulse wave $P_{BP}(t)$ produced in the artery pressed by the cuff 20, based on the actual cuff pulse wave signal SM detected by the pressure sensor 24; and the pulse wave analyzing means (the waveform, characteristic point determining means) 54 that analyzes the pressure pulse wave $P_{PB}(t)$ determined by the pulse wave determining means 52. Thus, the accurate pressure pulse wave $P_{BP}(t)$ is analyzed and accordingly an accurate evaluation of the circulatory organ of the subject or an accurate diagnosis on the same can be made.

In each of the illustrated embodiments, the pulse wave analyzing means 54 determines at least one of the maximum magnitude, the minimum magnitude, the rising point, the degree of sharpness % MAP, the maximum slope SLOPE of the rising portion, the pulse area, the augmentation index AI, and the ratio of maximum magnitude after change of posture of the subject to maximum magnitude before the change of posture, of heartbeat-synchronous pulse of the pressure pulse wave $P_{BP}(t)$ produced in the artery pressed by the cuff 20. Thus, the pulse wave analyzing means 54 can accurately determine at least one of the blood pressure, the pulse wave propagation velocity, the arteriosclerosis evaluation index, and the autonomic nerve evaluation value of. the subject.

Next, there will be described a second embodiment of the present invention that relates to a different method of determining a transfer function G(s) defining a transfer (or transmission) routine whose input is the pressure oscillation produced in the cuff 20 or the pressure pulsation produced in the brachial artery and whose output is the pressure detected by the pressure sensor 24. In the following description, the transfer function G(s) is determined using, e.g., auto regressive exogenous (ARX) model.

A relationship between input, i.e., no-delay cuff volumetric pulse wave $P_K(t)$ produced in the cuff 20 and output, i.e., cuff pulse wave signal SM(t) provided by the pressure sensor 24 can be expressed in various manners according to the ARX model. For example, this relationship can be represented by the following expression (5):

$$PK(S)+a_1PK(s-1)+\ldots+a_{na}PK(s-na)=SM(s)+b_1 SM(s-1)+b_2 SM(s-2)+\ldots+b_{nb}SM(s-nb) \quad \text{Expression (5)}$$

$$(1+a_1q^{-1}+\ldots+a_{na}q^{-na})PK(S)=(1+b_1q^{-1}+\ldots+b_{nb}q^{-nb})SM(s) \quad \text{Expression (6)}$$

$$SM(s)=(1+a_1q^{-1}+\ldots+a_{na}q^{-na})P_K(S)/(1+b_1q^{-1}+\ldots+b_{nb}q^{-nb}) \quad \text{Expression (7)}$$

$$G(s)=(1+a_1q^{-1}+\ldots+a_{na}q^{-na})/(1+b_1q^{-1}+\ldots+b_{nb}q^{nb}) \quad \text{Expression (8)}$$

In the expression (5), the symbol "s" indicates a time of detection of a prescribed reference point of a carotid pulse wave CW or a brachial pulse wave; the parenthesized numbers "(s)", "(s−1)", . . ., "(s−na)" indicate sampling times; $P_K(S)$ and SM(s) are respective sampling data of cuff volumetric pulse wave $P_K(t)$ and cuff pulse wave signal SM(t) that are iteratively obtained at a sampling period; and the symbols "na" and "nb" indicate respective sampling degrees that are experimentally determined in advance; for example, (na, nb)=(4, 6) or (10, 10). Next, the left and right sides of the expression (5) are modified using a time shift operator, q, to obtain the above indicated expression (6), which in turn provides the above indicated expression (7). Therefore, the transfer function G(s) can be expressed by the above indicated expression (8). In the case where the transfer function G(s) is expressed by the expression (8), the coefficients $a_1, a_{na}, b_1, \ldots, b_{bn}$ are determined as follows: The expression (5) is replaced with respective sampling data of cuff volumetric pulse wave $P_K(t)$ and cuff pulse wave signal SM(t) that are iteratively obtained from a living subject, so as to obtain an equation, and this operation is repeated to obtain a number of equations that is equal to, or greater than, the sum of respective total numbers na, nb of respective coefficients of the right and left sides of the expression (5), i.e., the number (na+nb). Those equations are subjected to least square method to determine the coefficients $a_{na}, \ldots, a_{na}, b_1, \ldots, b_{nb}$. For example, the relationship represented by the expression (7) may be stored in the ROM 42 employed in the first embodiment shown in FIG. 1, and the left hand of the expression (7) is replaced with the cuff pulse wave signal SM(t) detected by the pressure sensor 24 also employed in the first embodiment, so as to determine a no-delay cuff volumetric pulse wave $P_K(t)$ produced in the cuff 20.

While the present invention has been described in detail in its preferred embodiments by reference to the drawings, it is to be understood that the invention may otherwise be embodied.

For example, in each of the above-described first and second embodiments, the microphone 12 as a first sensor and the cuff 20 as a second sensor are worn on the heart and brachium 22 of the subject as the two different body portions of the subject, so as to measure the pulse wave propagation velocity PWV of the subject. However, the first and second sensors may be provided by a brachium cuff and an ankle cuff that are worn on a brachium and an ankle of a living subject, respectively. In the latter case, a pulse wave propagation velocity PWV of the subject is determined based on a time difference between respective signals obtained from the two cuffs.

In addition, the second sensor may be provided by a pressure pulse wave sensor that is adapted to be pressed on a radial artery via skin to detect a pressure pulse wave from the artery; or a photoelectric, finger-tip pulse wave sensor that is adapted to be worn on the tip of a finger to detect a photoelectric pulse wave from the finger.

It is to be understood that the present invention may be embodied with other changes, improvements and modifications that may occur to a person skilled in the art without departing from the spirit and scope of the invention defined in the appended claims.

What is claimed is:

1. An apparatus for obtaining a cuff volumetric pulse wave, comprising:
    a cuff adapted to be worn on a limb of a living subject so that a pressure pulsation is produced in the cuff;
    a pressure sensor which is connected to the cuff, and which detects, as an actual cuff volumetric pulse wave, a pressure oscillation transmitted thereto from the cuff;
    an inverse transfer function memory which stores an inverse transfer function corresponding to a transfer function between pressure pulsation as input and pressure oscillation as output; and
    a cuff volumetric pulse wave determining means for determining a no-delay cuff volumetric pulse wave having substantially no delay of transmission based on the actual cuff volumetric pulse wave detected by the pressure sensor and the inverse transfer function stored by the inverse transfer function memory.

2. An apparatus for analyzing a cuff volumetric pulse wave obtained from a living subject, comprising:
    the cuff volumetric pulse wave obtaining apparatus according to claim 1; and
    a pulse wave analyzing means for analyzing the no-delay cuff volumetric pulse wave obtained by the cuff volumetric pulse wave obtaining apparatus, and thereby determining at least one of a blood pressure, a pulse wave propagation velocity, an arteriosclerosis evaluation index, and an autonomic nerve evaluation value of the subject.

3. The apparatus according to claim 2, wherein the pulse wave analyzing means determines at least one of a maximum magnitude, a minimum magnitude, a rising point, a degree of sharpness % MAP, a maximum slope SLOPE of a rising portion, an area, an augmentation index AI, and a ratio of a maximum magnitude after change of posture of the subject to a maximum magnitude before the change of posture, of a heartbeat-synchronous pulse of the no-delay cuff volumetric pulse wave determined by the cuff volumetric pulse wave determining means.

4. A method of obtaining a cuff volumetric pulse wave with an apparatus including a cuff adapted to be worn on a limb of a living subject so that a pressure pulsation is produced in the cuff, a pressure sensor which is connected to the cuff, and which detects, as an actual cuff volumetric pulse wave, a pressure oscillation transmitted thereto from the cuff, an inverse transfer function memory which stores an inverse transfer function corresponding to a transfer function between pressure pulsation as input and pressure oscillation as output, and a cuff volumetric pulse wave determining means for determining a no-delay cuff volumetric pulse wave having substantially no delay of transmission based on the actual cuff volumetric pulse wave detected by the pressure sensor and the inverse transfer function stored by the inverse transfer function memory, the method comprising:

(a) a step of determining the inverse transfer function corresponding to the transfer function, and storing the determined inverse transfer function in the inverse transfer function memory; and (b) a step of determining, using the inverse transfer function stored by the inverse transfer function memory, the no-delay cuff volumetric pulse wave having substantially no delay of transmission, based on the actual cuff volumetric pulse wave detected by the pressure sensor.

5. A method of obtaining a cuff volumetric pulse wave with an apparatus including a cuff adapted to be worn on a limb of a living subject so that a pressure pulsation is produced in the cuff, a pressure sensor which is connected to the cuff, and which detects, as an actual cuff volumetric pulse wave, a pressure oscillation transmitted thereto from the cuff, an inverse transfer function memory which stores an inverse transfer function corresponding to a transfer function between pressure pulsation as input and pressure oscillation as output, a cuff volumetric pulse wave determining means for determining a no-delay cuff volumetric pulse wave having substantially no delay of transmission based on the actual cuff volumetric pulse wave detected by the pressure sensor and the inverse transfer function stored by the inverse transfer function memory, and a pulse wave analyzing means for analyzing the no-delay cuff volumetric pulse wave determined by the cuff volumetric pulse wave determining means, the method comprising:

(a) a step of determining the inverse transfer function corresponding to the transfer function, and storing the determined inverse transfer function in the inverse transfer function memory;

(b) a step of determining, using the inverse transfer function stored by the inverse transfer function memory, the no-delay cuff volumetric pulse wave having substantially no delay of transmission, based on the actual cuff volumetric pulse wave detected by the pressure sensor; and (c) a step of analyzing the determined no-delay cuff volumetric pulse wave, and thereby determining at least one of a blood pressure, a pulse wave propagation velocity, an arteriosclerosis evaluation index, and an autonomic nerve evaluation value of the subject.

6. The method according to claim 5, further comprising: determining with the pulse wave analyzing means at least one of a maximum magnitude, a minimum magnitude, a rising point, a degree of sharpness % MAP, a maximum slope SLOPE of a rising portion, an area, an augmentation index AI, and a ratio of a maximum magnitude after change of posture of the subject to a maximum magnitude before the change of posture, of a heartbeat-synchronous pulse of the no-delay cuff volumetric pulse wave determined by the cuff volumetric pulse wave determining means.

7. An apparatus for obtaining a pressure pulse wave, comprising:

a cuff adapted to be worn on a limb of a living subject so as to press an artery of the limb;

a pressure sensor which is connected to the cuff, and which detects, as a cuff volumetric pulse wave, a pressure oscillation transmitted thereto from the cuff;

an inverse transfer function memory which stores an inverse transfer function corresponding to a transfer function between intra-arterial pressure as input and pressure oscillation as output; and a pressure pulse wave determining means for determining a pressure pulse wave produced in the artery, based on the cuff volumetric pulse wave detected by the pressure sensor and the inverse transfer function stored by the inverse transfer function memory.

8. An apparatus for analyzing a pressure pulse wave obtained from a living subject, comprising:

the pressure pulse wave obtaining apparatus according to claim 7; and a pulse wave analyzing means for analyzing the pressure pulse wave produced in the artery, and obtained by the pressure pulse wave obtaining apparatus, and thereby determining at least one of a blood pressure, a pulse wave propagation velocity, an arteriosclerosis evaluation index, and an autonomic nerve evaluation value of the subject.

9. The apparatus according to claim 8, wherein the pulse wave analyzing means determines at least one of a maximum magnitude, a minimum magnitude, a rising point, a degree of sharpness % MAP, a maximum slope SLOPE of a rising portion, an area, an augmentation index AI, and a ratio of a maximum magnitude after change of posture of the subject to a maximum magnitude before the change of posture, of a heartbeat-synchronous pulse of the pressure pulse wave determined by the pressure pulse wave determining means.

10. A method of obtaining a pressure pulse wave with an apparatus including a cuff adapted to be worn on a limb of a living subject so as to press an artery of the limb, a pressure sensor which is connected to the cuff, and which detects, as a cuff volumetric pulse wave, a pressure oscillation transmitted thereto from the cuff, an inverse transfer function memory which stores an inverse transfer function corresponding to a transfer function between intra-artery pressure as input and pressure oscillation as output, and a pressure pulse wave determining means for determining a pressure pulse wave produced in the artery, based on the cuff volumetric pulse wave detected by the pressure sensor and the inverse transfer function stored by the inverse transfer function memory, the method comprising:

(a) a step of determining the inverse transfer function corresponding to the transfer function, and storing the determined inverse transfer function in the inverse transfer function memory; and (b) a step of determining, using the inverse transfer function stored by the inverse transfer function memory, the pressure pulse wave produced in the artery, based on the cuff volumetric pulse wave detected by the pressure sensor.

11. A method of obtaining a pressure pulse wave with an apparatus including a cuff adapted to be worn on a limb of a living subject so as to press an artery of the limb,
- a pressure sensor which is connected to the cuff, and which detects, as a cuff volumetric pulse wave, a pressure oscillation transmitted thereto from the cuff,
- an inverse transfer function memory which stores an inverse transfer function corresponding to a transfer function between intra-arterial pressure as input and pressure oscillation as output,
- a pressure pulse wave determining means for determining a pressure pulse wave produced in the artery, based on the cuff volumetric pulse wave detected by the pressure sensor and the inverse transfer function stored by the inverse transfer function memory, and
- a pulse wave analyzing means for analyzing the pressure pulse wave determined by the pressure pulse wave determining means, the method comprising:
  - (a) a step of determining the inverse transfer function corresponding to the transfer function, and storing the determined inverse transfer function in the inverse transfer function memory;
  - (b) a step of determining, using the inverse transfer function stored by the inverse transfer function memory, the pressure pulse wave produced in the artery, based on the cuff volumetric pulse wave detected by the pressure sensor; and
  - (c) a step of analyzing the determined pressure pulse wave, and thereby determining at least one of a blood pressure, a pulse wave propagation velocity, an arteriosclerosis evaluation index, and an autonomic nerve evaluation value of the subject.

12. The method according to claim 11, further comprising:
- determining with the pulse wave analyzing means at least one of a maximum magnitude, a minimum magnitude, a rising point, a degree of sharpness % MAP, a maximum slope SLOPE of a rising portion, an area, an augmentation index AI, and a ratio of a maximum magnitude after change of posture of the subject to a maximum magnitude before the change of posture, of a heartbeat-synchronous pulse of the pressure pulse wave determined by the pressure pulse wave determining means.

13. A method of obtaining a cuff volumetric pulse wave with an apparatus including a cuff adapted to be worn on a limb of a living subject so that a pressure pulsation is produced in the cuff,
- a pressure sensor which is connected to the cuff, and which detects, as an actual cuff volumetric pulse wave, a pressure oscillation transmitted thereto from the cuff,
- an inverse transfer function memory which stores an inverse transfer function corresponding to a transfer function between pressure pulsation as input and pressure oscillation as output, and
- a cuff volumetric pulse wave determining device which determines a no-delay cuff volumetric pulse wave having substantially no delay of transmission based on the actual cuff volumetric pulse wave detected by the pressure sensor and the inverse transfer function stored by the inverse transfer function memory, the method comprising:
  - (a) a step of determining the inverse transfer function corresponding to the transfer function, and storing the determined inverse transfer function in the inverse transfer function memory; and
  - (b) a step of determining, using the inverse transfer function stored by the inverse transfer function memory, the no-delay cuff volumetric pulse wave having substantially no delay of transmission, based on the actual cuff volumetric pulse wave detected by the pressure sensor.

14. A method of obtaining a cuff volumetric pulse wave, with an apparatus including a cuff adapted to be worn on a limb of a living subject so that a pressure pulsation is produced in the cuff,
- a pressure sensor which is connected to the cuff, and which detects, as an actual cuff volumetric pulse wave, a pressure oscillation transmitted thereto from the cuff,
- an inverse transfer function memory which stores an inverse transfer function corresponding to a transfer function between pressure pulsation as input and pressure oscillation as output,
- a cuff volumetric pulse wave determining device which determines a no-delay cuff volumetric pulse wave having substantially no delay of transmission based on the actual cuff volumetric pulse wave detected by the pressure sensor and the inverse transfer function stored by the inverse transfer function memory, and
- a pulse wave analyzing device which analyzes the no-delay cuff volumetric pulse wave determined by the cuff volumetric pulse wave determining device, the method comprising:
  - (a) a step of determining the inverse transfer function corresponding to the transfer function, and storing the determined inverse transfer function in the inverse transfer function memory;
  - (b) a step of determining, using the inverse transfer function stored by the inverse transfer function memory, the no-delay cuff volumetric pulse wave having substantially no delay of transmission, based on the actual cuff volumetric pulse wave detected by the pressure sensor; and
  - (c) a step of analyzing the determined no-delay cuff volumetric pulse wave, and thereby determining at least one of a blood pressure, a pulse wave propagation velocity, an arteriosclerosis evaluation index, and an autonomic nerve evaluation value of the subject.

15. A method of obtaining a pressure pulse wave with an apparatus including a cuff adapted to be worn on a limb of a living subject so as to press an artery of the limb,
- a pressure sensor which is connected to the cuff, and which detects, as a cuff volumetric pulse wave, a pressure oscillation transmitted thereto from the cuff,
- an inverse transfer function memory which stores an inverse transfer function corresponding to a transfer function between intra-artery pressure as input and pressure oscillation as output, and
- a pressure pulse wave determining device which determines a pressure pulse wave produced in the artery, based on the cuff volumetric pulse wave detected by the pressure sensor and the inverse transfer function stored by the inverse transfer function memory, the method comprising:
  - (a) a step of determining the inverse transfer function corresponding to the transfer function, and storing the determined inverse transfer function in the inverse transfer function memory; and
  - (b) a step of determining, using the inverse transfer function stored by the inverse transfer function memory, the pressure pulse wave produced in the artery, based on the cuff volumetric pulse wave detected by the pressure sensor.

16. A method of obtaining a pressure pulse wave with an apparatus comprising a cuff adapted to be worn on a limb of a living subject so as to press an artery of the limb,
- a pressure sensor which is connected to the cuff, and which detects, as a cuff volumetric pulse wave, a pressure oscillation transmitted thereto from the cuff,
- an inverse transfer function memory which stores an inverse transfer function corresponding to a transfer function between intra-arterial pressure as input and pressure oscillation as output,
- a pressure pulse wave determining device which determines a pressure pulse wave produced in the artery, based on the cuff volumetric pulse wave detected by the pressure sensor and the inverse transfer function stored by the inverse transfer function memory, and
- a pulse wave analyzing device which analyzes the pressure pulse wave determined by the pressure pulse wave determining device, the method comprising:

(a) a step of determining the inverse transfer function corresponding to the transfer function, and storing the determined inverse transfer function in the inverse transfer function memory;

(b) a step of determining, using the inverse transfer function stored by the inverse transfer function memory, the pressure pulse wave produced in the artery, based on the cuff volumetric pulse wave detected by the pressure sensor; and (c) a step of analyzing the determined pressure pulse wave, and thereby determining at least one of a blood pressure, a pulse wave propagation velocity, an arteriosclerosis evaluation index, and an autonomic nerve evaluation value of the subject.

* * * * *